(12) United States Patent
Klimes et al.

(10) Patent No.: US 7,192,515 B2
(45) Date of Patent: Mar. 20, 2007

(54) MOBILE HAND-HELD APPARATUS WITH REUSABLE BIOSENSOR

(75) Inventors: Norbert Klimes, Berlin (DE); Dorothea Pfeiffer, Berlin (DE); Jan Szeponik, Berlin (DE); Frieder Scheller, Zepernick (DE); Fred Held, Hamburg (DE)

(73) Assignee: ABT Advanced Bioanalytical Technology GmbH, Radeberg (DE)

( * ) Notice: Subject to any disclaimer, the term of this patent is extended or adjusted under 35 U.S.C. 154(b) by 147 days.

(21) Appl. No.: 10/182,618

(22) PCT Filed: Jan. 5, 2001

(86) PCT No.: PCT/DE01/00002

§ 371 (c)(1),
(2), (4) Date: Sep. 13, 2002

(87) PCT Pub. No.: WO01/50126

PCT Pub. Date: Jul. 12, 2001

(65) Prior Publication Data
US 2003/0029231 A1 Feb. 13, 2003

(30) Foreign Application Priority Data
Jan. 5, 2000 (DE) .............................. 200 00 122

(51) Int. Cl.
*G01N 33/487* (2006.01)
(52) U.S. Cl. ................ 205/792; 205/775; 204/903.01; 204/409
(58) Field of Classification Search ................ 204/400, 204/403, 409, 415, 403.01; 600/300, 308, 600/309, 345, 352, 366, 368; 73/863, 864.81, 73/864.83; 205/775, 792
See application file for complete search history.

(56) References Cited

U.S. PATENT DOCUMENTS

| | | | | |
|---|---|---|---|---|
| 3,874,850 A | * | 4/1975 | Sorensen et al. | 436/50 |
| 4,202,747 A | * | 5/1980 | Buzza et al. | 204/411 |
| 5,535,744 A | * | 7/1996 | DiNino | 600/345 |
| 6,037,178 A | * | 3/2000 | Leiner et al. | 436/50 |
| 6,171,238 B1 | * | 1/2001 | Klimes et al. | 600/345 |

FOREIGN PATENT DOCUMENTS

| | | |
|---|---|---|
| DE | 295 11 566 U | 11/1995 |
| DE | 200 00 122 U | 4/2000 |
| EP | 0 460 343 A | 12/1991 |
| EP | 0 754 944 A | 1/1997 |
| WO | WO 9703355 A1 * | 1/1997 |
| WO | 97 43640 A | 11/1997 |

* cited by examiner

*Primary Examiner*—Kaj K. Olsen
(74) *Attorney, Agent, or Firm*—Buchanan Ingersoll & Rooney PC

(57) ABSTRACT

Mobile hand-held apparatus with reusable biosensor, in particular for the local determination of original biological solutions, marked by a functional wheel with valve and pump function, an amperometric biosensor, a measuring cell, supply and waste bags for fresh and waste system solution, a pump, a hose transport system, a sample opening and a sample canal, a sealing lever for sensor exchange, a display, operating elements, a 9 V accumulator, a solar cell, a control unit for signal processing and the whole measuring process and a case.

17 Claims, 2 Drawing Sheets

MOBILE HAND-HELD APPARATUS WITH REUSABLE BIOSENSOR

This application is the national phase under 35 U.S.C. § 371 of PCT International Application no. PCT/DE01/00002 which has an International filing date of Jan. 5, 2001, which designated the United States of America.

BACKGROUND OF THE INVENTION

1. Field of the Invention

The invention concerns a hand-held apparatus for the examination of biological liquids such as whole blood, liquor, urine and serum by electrochemical biosensors without conducting costly preceding analysis.

2. Discussion of the Prior Art

For a fairly long time biosensors have been used as sensitive and selective detection methods in analyses, and in particular in medical diagnostics. For this purpose, respective biosensors are installed in analysers which permit a fast, inexpensive and notably proper examination of the respective parameters in central laboratories where many samples have to be examined. This requires, as a rule, a sample throughput of 80–180/h.

The analysers are based on various principles. For the most part, they are operated with a continuous air segmented flow of the respective, highly diluted laboratory samples, i.e. This method requires the preparation of the solutions to be examined (e.g. whole blood) with a dilution of the analysis material being required. It is very costly to analyse individual samples using this equipment as the efficiency of analysers becomes effective only in the case of a great number of Prüfgeräte-Werk Medingen GmbH, EBIO (Eppendorf® from Eppendorf-Netheler-Hinz GmbH).

Furthermore, instructions are known to measure individual samples also without preceding analyses. which, however, are very immovable owing to a high integrated measuring comfort, thus being unsuited for a local application (YSI 2300 STAT of YSI Incorporated and STAT Profile PLUS of NOVA BIOMEDICAL GmbH).

For the time being, commercially available mobile systems with integrated biosensors are too expensive owing to the high measuring comfort (internal calibration). They require too much maintenance and are operated with excessively long transport ways for the sample to be measured. For this reason, in addition to a comparatively high price, delays and pollution will result which have detrimental effects on the quality of analysing.

All measuring systems applied locally to determine parameters such as glucose and lactate are at present based on non-reusable consumables (test strips, photometric; strip electrode, amperometric). Thus the analysis is determined by the price of the test strip and the test strip can not be calibrated as it may only be used once.

The 'mobile hand-held device with biosensor' of GM 29511566.1 represents a significant improvement. That instrument is based on a reusable biosensor allowing the calibration of the sensor resulting in an improved quality of analysis as compared to the disposable test strips. Further advantages result from lower costs of the analysis.

As compared to the high quality results of laboratory analysis the mobile hand-held device of GM 29511566.1 is characterized by mobility and constant quality, i.e., decentralized analysis of high quality is possible independent of the laboratory using this instrument.

However, the technical realization of the measuring procedure has become disadvantageous during practical use. The operation of two different operation elements in parallel is complicated and may cause handling errors.

That is why it was the task of the invention to provide a technical solution for providing a locally applicable equipment for the examination of blood, urine, liquor without preceding analyses being carried out and a re-usable biosensor which is marked by a high quality of analysis, a low price and a simple operation procedure.

The task will be solved by the construction of a hand-held apparatus with linear operation.

SUMMARY OF THE INVENTION

The hand-held apparatus consists of a functional wheel with valve and pump function, an exchangeable electrochemical biosensor, a system solution supply bag, a waste bag, a pump, a hose transport system, four operating elements, a display and a control unit for signal recording and the whole process that is supplied by a solar cell and a 9 V accumulator. The equipment works with a temperature compensation. Thus, modified sensitivities of the biosensor are compensated through variations of the ambient temperature in the range between 15° C. and 35° C. on the basis of a signal-temperature function.

Welded PE foils are preferentially used for the system solution bag and the waste bag, with the storage volume totalling approx. ⅓ and the waste volume approx. ⅔ of the total volume. The two bags are welded to each other an arranged one above the other. The bags are opened when being installed in the hand-held apparatus by means of a hollow needle. When putting in a new supply bag the second half of the PE bag will be empty. In the same way as the stock will be consumed for rinsing the measuring cell, the waste bag will be filled. After having consumed the system solution completely, the whole bag will be disposed of.

The easy exchangeable electrochemical biosensor is a Pt-Ag/AgCl electrode which may register various substances in accordance with the biomolecule used.

To execute a measurement the functional wheel will be moved from idle position A (5) (READY) to position B (6) (SAMPLE) by moving the wheel clockwise, thus bringing the system into the state 'ready for measurement'.

The sample to be analysed will be supplied with adjusting the freshly taken sample in a capillary tube to the sample opening of the hand-held apparatus which is directly above the biosensor. Subsequently the functional wheel is moved to position C (7) (BUSY) and the sample to be measured is transported by it in front of the biosensor. After the measurement takes place, the operator is requested by the display reading to take off the capillary tube and to rinse the system. The capillary tube is taken off by the operator. By moving the functional wheel to position A the sensor is rinsed and the measuring value is indicated. The measuring value will be shown in the display until the next measurement is taken. The reading "READY FOR USE" is regarded to be a confirmation that the rinsing is completed and the device is again ready for use.

A hose pump is preferentially used as the pump which is driven by manual or electric energy.

The four operating elements will be responsible for the following functions:

B1: on;

B2: menu functions;

B3: set key; and

B4: enter key.

Power supply will be realized by an internal 9 V accumulator that will be recharged preferably by a solar cell or alternatively by an external supply.

Depending on the biomolecule used, a biosensor has a limited lifetime which totals, in general, 10 to 30 days. The user will be shown the expiration of lifetime on the display. Upon expiration of its service life, the biosensor will be replaced by a new one.

The biosensor is replaced by unlocking the respective sealing lever (9), taking out the worn-out biosensor (11) and simply placing a new biosensor. By the information on the display the user will be informed of the steps necessary to be taken to make the new biosensor operative.

Signal recording and the whole process are controlled through a control unit. The whole process involves the beginning of signal recording (start), the end of signal recording, filing and storing of measured values, the calibration of the equipment and display information for the operator regarding the steps.

The hand-held equipment in conformity with the invention permits carrying out a minimum of 500 measurements without replacing the supply bag. A special advantage is that the equipment is usable in a temperature range between 15° C. and 35° C., independent of its place and time of use. The weight of the equiment is less than 500 g.

BRIEF DESCRIPTION OF THE DRAWINGS

The invention is explained in greater detail by means of the following examples and drawings.

DETAILED DESCRIPTION OF THE PREFERRED EMBODIMENTS

Figure 1:
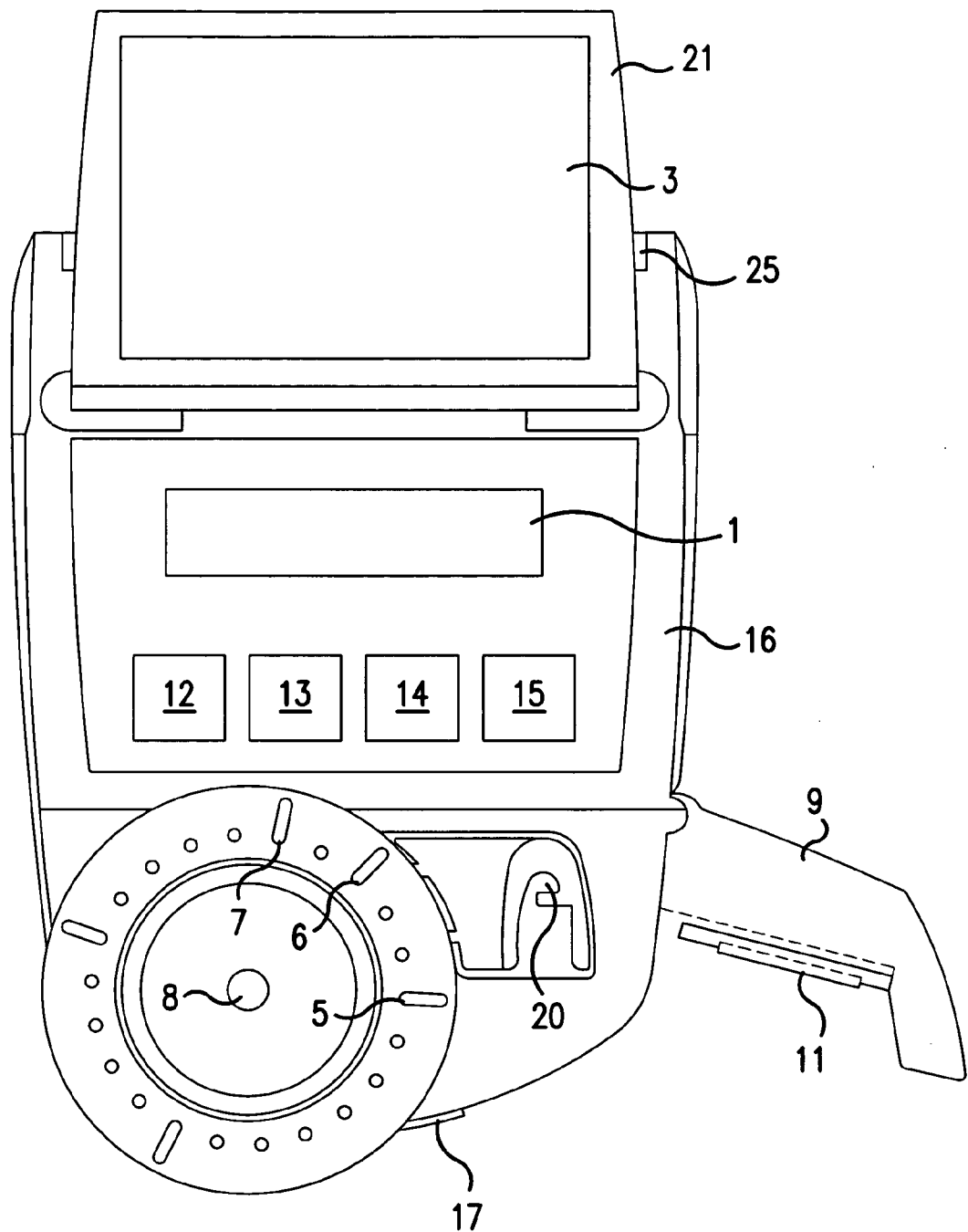
FIG. 1 is an overall view of the hand-held equipment

The hand-held apparatus in conformity with FIG. 1 serves the examination of whole blood, liquor, tissue fluid, urine, serum, plasma, food samples as well as water samples as regards metabolites such as e.g. glucose, lactate; yet also nutrients and products of food and fermentation industries such as e.g. lactose, ascorbic acid, malic acid and various amino acids.

Figure 2:
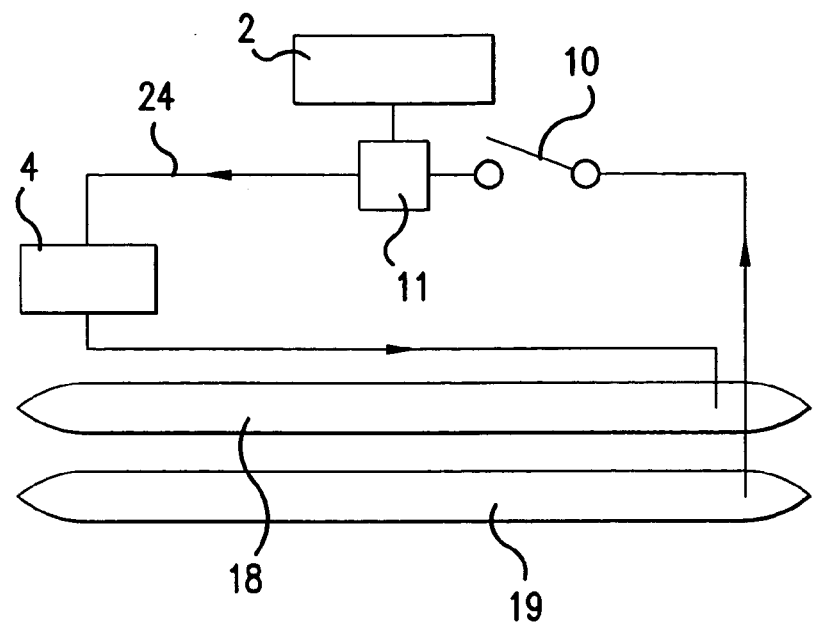
FIG. 2 is a basic diagram of the apparatus and the arrangement of the supply and waste bag
Figure 2:
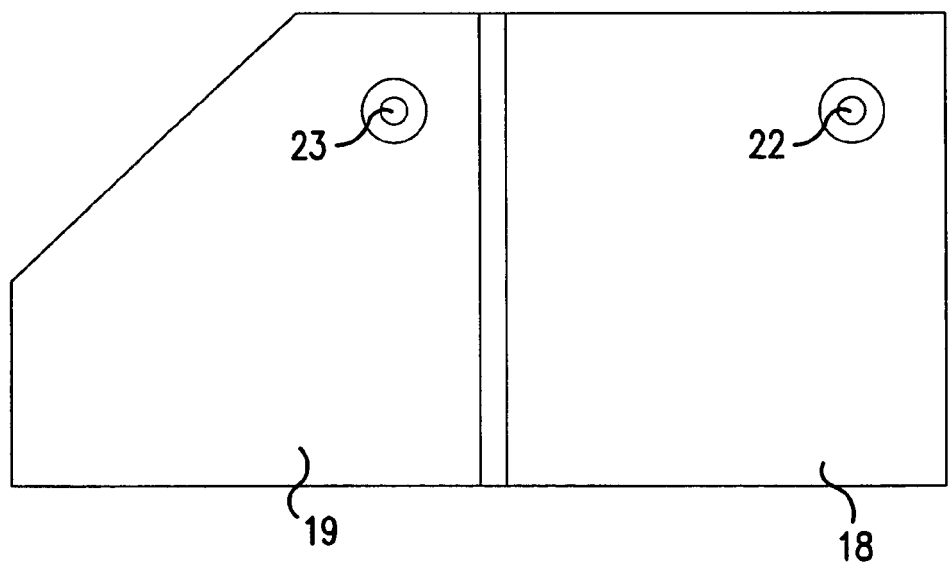

In FIGS. 1 and 2 the structure of such an instrument is demonstrated in principle. The process of a measurement is described in the following. The idle and stand-by position of the instrument is position A (5) (READY) of the functional wheel (8). After switching on the instrument by B1 (12) the functional wheel (8) is moved to position B (6). After the operator is requested by the display (1) to place the sample into the instrument, the operator places the sample using a capillary tube into the sample opening (20) of the hand-held apparatus and moves the functional wheel (8) to position C (7).

After completing measurement the operator is requested to take away the capillary and to rinse the system. For that purpose the capillary is taken out from the sample opening (20) and the functional wheel (8) is moved to position A (5). By that procedure I) the measured value will be shown on the display (1) and II) systemic solution is moved from the buffer supply (19) via the valve system through the sensor containing measuring chamber into the waste bag (18). The contact of the biosensor with the buffer solution results in the rinsing of the sensor. The operator is informed on the termination of the rinsing procedure by "ready for use" on display (1). Thus, the hand-held apparatus will be again ready for measuring and the following measurement will be effected according to the same scheme.

The biosensor (11) is exchanged after expiration of its lifetime (which is shown to the operator on display 1). To this end, the sealing lever (9) has to be opened and the old sensor exchanged. After that the sealing lever (9) and the flow system is consequently closed again. By the information on the display the user will be informed of the steps necessary to be taken to make the new biosensor operative.

Reference numerals are:
1. display;
2. control unit;
3. solar cell with a 9V accumulator;
4. pump;
5. position A of the functional wheel;
6. position B of the functional wheel;
7. position C of the functional wheel;
8. functional wheel with valve and pump function;
9. sealing lever;
10. valve;
11. (FIG. 1) biosensor outride of measuring cell. It will be moved inside the measuring cell by shutting the sealing lever (9) (FIG. 2) biosensor inside the measuring cell;
12. operating element B1;
13. operating element B2;
14. operating element B3;
15. operating element B4;
16. case;
17. spring for sealing lever;
18. waste bag;
19. supply bag;
20. sample opening (opening of the sample canal);
21. cover;
22. seal for waste bag;
23. seal for supply bag; and
24. hose transport system
25. 9V accumulator.

The invention claimed is:

1. A handheld apparatus comprising:
a display;
a sensor unit for receiving a biosensor; and
a selector unit for switching between a first, second, and third mode of operation, the first mode being a ready mode, the second mode being a sampling mode, and the third mode being a cleaning mode, wherein the selector unit is a functional wheel that controls both a valve and a pump,
wherein, during the second mode of operation, a sample is provided to the sensor unit for measuring the sample and provided a measurement value to the display, and
wherein the measurement value is only displayed on the display after the selector unit is switched to the cleaning mode, the cleaning mode initiating a pumping action to pump a solution to clean at least the biosensor in the sensor unit.

2. The apparatus according to claim 1, wherein the biosensor is arranged directly below a sample opening, the sample opening being provided in the sensor unit.

3. The apparatus according to claim 1, wherein the pumping action is performed by a pump that is operated by hand or by electric energy.

4. The apparatus according to claim 1, wherein the solution is pumped from a supply bag to a waste bag, wherein welded PE foil is used for the supply bag and the waste bag, and wherein the supply bag and waste bag are welded to one another and arranged one above the other and will be jointly disposed after the solution is depleted from the supply bag.

5. The apparatus according to claim 1, further comprising a power supply that has a chargeable accumulator that is recharged by a solar cell or by a supply unit.

6. The apparatus according to claim 1, wherein a weight of the apparatus is less than 500 g.

7. The apparatus according to claim 1, wherein the measurement value is only displayed on the display after the selector unit is switched to the cleaning mode and after the selector unit is switched to the ready mode.

8. The apparatus according to claim 1, wherein the biosensor is an amperometric biosensor, and wherein the solution is pumped from a supply bag to a waste bag through a hose transport system.

9. The apparatus according to claim 1, wherein the biosensor is replaced via operation of a sealing lever.

10. The apparatus according to claim 1, further comprising a solar cell for supplying operating power to the apparatus.

11. The apparatus according to claim 1, further comprising a control unit for processing the measurement value and for controlling the apparatus on the basis of the first, second, or third mode of operation.

12. The apparatus according to claim 1, wherein the biosensor is a reusable biosensor.

13. The apparatus according to claim 12, wherein the reusable biosensor is integrated into the apparatus via a replaceable connection.

14. The apparatus according to claim 1, wherein the selector unit is provided internally or externally to the apparatus.

15. The apparatus according to claim 1, wherein the selector unit is attached to the apparatus.

16. A method for measuring a sample, the method comprising the steps of:
providing the sample to a sensor unit, the sensor unit being capable of receiving a biosensor, the sensor unit providing a measurement value to a display of a handheld apparatus; and
switching a selector unit from a first mode of operation to a second mode of operation and third mode of operation, the first mode being a ready mode, the second mode being a sampling mode,
measuring a sample in said sampling mode and obtaining a first measurement value,
switching said selector unit from said second mode of operation to a third mode of operation said third mode being a cleaning mode,
wherein the first measurement value is only displayed on the display after the selector unit is switched to the cleaning mode, the cleaning mode initiating a pumping action to pump a solution to clean at least the biosensor in the sensor unit.

17. Mobile hand-held equipment with reusable biosensor, in particular for the local determination of original biological solutions, marked by
a functional wheel with valve and pump function (8),
an amperometric biosensor (11),
a measuring cell,
supply (19) and waste bags (18) for fresh and waste system solution
a pump (4),
a hose transport system,
a sample opening (20) and a sample canal,
a sealing lever for sensor exchange (9),
a display (1),
4 operating elements (12, 13, 14, 15),
a 9 V accumulator,
a solar cell (3),
a control unit for signal processing and the whole measuring process (2) and
a case (16).

* * * * *